(12) United States Patent
Williams et al.

(10) Patent No.: US 7,186,883 B2
(45) Date of Patent: *Mar. 6, 2007

(54) IN VITRO PROPAGATION OF EMBRYONIC STEM CELLS

(75) Inventors: Robert Lindsay Williams, Warrandyte (AU); Nicholas Martin Gough, North Balwyn (AU); Douglas James Hilton, Warrandyte (AU)

(73) Assignee: Zenyth Operations Pty Ltd., Victoria (AU)

( * ) Notice: Subject to any disclaimer, the term of this patent is extended or adjusted under 35 U.S.C. 154(b) by 383 days.

This patent is subject to a terminal disclaimer.

(21) Appl. No.: 10/121,220

(22) Filed: Apr. 12, 2002

(65) Prior Publication Data

US 2003/0064512 A1    Apr. 3, 2003

Related U.S. Application Data

(63) Continuation of application No. 09/887,694, filed on May 2, 2001, now abandoned, which is a continuation of application No. 09/584,026, filed on May 30, 2000, now abandoned, which is a continuation of application No. 09/050,457, filed on Mar. 30, 1998, now abandoned, which is a continuation of application No. 08/278,561, filed on Jul. 21, 1994, now abandoned, which is a continuation of application No. 07/924,809, filed on Aug. 4, 1992, now abandoned, which is a continuation of application No. 07/477,960, filed on May 31, 1990, now Pat. No. 5,166,065.

(30) Foreign Application Priority Data

Aug. 4, 1988  (AU) .................................. PJ 9644/88

(51) Int. Cl.
*C12N 15/01* (2006.01)
(52) U.S. Cl. .............................. 800/21; 800/18; 800/25
(58) Field of Classification Search .................... 800/18
See application file for complete search history.

(56) References Cited

U.S. PATENT DOCUMENTS

| 4,736,866 A | * | 4/1988 | Leder et al. ................. 800/10 |
| 5,166,065 A | | 11/1992 | Williams et al. |
| 5,187,077 A | | 2/1993 | Gearing et al. |
| 5,340,740 A | | 8/1994 | Petitte et al. |
| 5,366,888 A | | 11/1994 | Fry et al. |
| 5,843,780 A | * | 12/1998 | Thomson ................. 435/363 |
| 6,200,806 B1 | * | 3/2001 | Thomson ................. 435/366 |

OTHER PUBLICATIONS

Martin (1981) "Isolation of a Pluripotent Cell Line from Early Mouse Embryos Cultured in Medium Conditioned by Teratocarcinoma Stem Cells" Proc. Natl. Acad. Sci. USA 78, 7634-7638.
Experimental approaches to mammalian embryonic development, edited by Robert & Pederson, Chapter 15, pp. 475-508 (1986).
Handyside, et al. (1987) "Towards the Isolation of Embryonal Stem Cell Lines from the Sheep" Roux's Arch. Dev. Biol. 196, 185-190.
Smith, et al. (1987) "Buffalo Rat Liver Cells Produce a Diffusible Activity which Inhibits the Differentiation of Murine Embryonal Carcinoma and Embryonic Stem Cells" Developmental Biology 121, 1-9.
Williams et al. (1988), Nature, 336: 684-687.
Health et al. (1988), J. Cell Sci. Suppl., 10: 257-266.
Doetschman, et al. (1988) "Establishment of Hamster Blastocyst-Derived Embryonic Stem (ES) Cells" Developmental Biology 127, 224-227.
Moreau et al. (1988), Nature, 336: 690-692.
Giugh et al. (1989), Reprod. Fert. Dev., vol. 1, pp. 281-288.
Nicholas, (1990) Development, 110:1341-1348.
Pease et al. (1990), Developmental Biology, 141: 344-352.
Pease et al. (1990), Experimental Cell Research, 190: 209-211.
Notarianni et al. (1991), J. Reprod., Fert., Suppl. 43: 255-260.
Saito et al., (1992) Roux's Arch Dev. Biol., vol. 201, pp. 134-141.
Sukoyan et al. (1992), Molecular Reproduction & Development, vol. 33, pp. 418,431.
Fry, R.C. (1992), Reprod. Fert. Dev., 4:449-458.
Yang et al. (1992), Theriogenology, vol. 38, pp. 315-335.
Fry et al. (1992), Biology of Reproduction, 46:470-474.
Scharfenstein, et al., (1996)"Identification, Isolation and Culture of Pluripotent Cells from the Porcine Inner Cell Mass" J. Anim. Breed. Genet. 113:427-436.
Wheeler, et al. (1994) Reprod. Fertil. Dev. 6:563-568.
Evans, et al. (1990) "Derivation and Preliminary Characterization of Pluripotent Cell Lines from Porcine and Bovine Blastocysts", Theriogenology 33:125-128.

(Continued)

*Primary Examiner*—Joseph Woitach
(74) *Attorney, Agent, or Firm*—Scully, Scott, Murphy & Presser, P.C.

(57) ABSTRACT

The present invention relates to the use of leukemia inhibitory factor (LIF) in the isolation and propagation of embryonic stem cells in vitro.

6 Claims, 3 Drawing Sheets

OTHER PUBLICATIONS

Piedrahita, et al. (1990) "Influence of Feeder Layer Type on the Efficiency of Isolation of Porcine Embryo Derived Cell Lines", Theriogenology 34:865-877.

Piedrahita, et al. (1990) "On the Isolation of Embtryonic Stem Cells: Comparative Behavior or Murine, Porcine and Ovine Embryos", Theriogenology 34:879-901.

Strojek, et al. (1990) "A Method for Cultivating Morphologenically Undifferentiated Embryonic Stem Cells from Porcine Blastocysts", Theriogenology 33:901-913; and.

Bongso, et al. (1994) "Isolation and Culture of Inner Cell Mass Cells from Human Blastocysts", Human Reprod. 9:2110.

* cited by examiner

IN VITRO PROPAGATION OF EMBRYONIC STEM CELLS

CROSS REFERENCE TO RELATED APPLICATIONS

The present application is a continuation of application Ser. No. 09/887,694 filed May 2, 2001 now abandoned which is a continuation of U.S. patent application Ser. No. 09/584,026 filed May 30, 2000 now abandoned which is a continuation of U.S. patent application Ser. No. 09/050,457 filed Mar. 30, 1998 now abandoned which is a continuation of U.S. patent application Ser. No. 08/278,561 filed Jul. 21, 1994 now abandoned which is a file wrapper continuation application of Ser. No. 07/924,809 filed Aug. 4, 1992 now abandoned which is a continuation of U.S. patent application Ser. No. 07/477,960 filed May 31, 1990 now U.S. Pat. No. 5,166,065.

This invention relates to the use of a previously discovered and characterised molecule, leukaemia inhibitory factor (LIF), in the isolation and propagation of embryonic stem cells in vitro.

Embryonic stem (ES) cells, the pluripotent outgrowths of blastocysts, can be cultured and manipulated in vitro and then returned to the embryonic environment to contribute normally to all tissues including the germline (for review see Robertson, E. J. (1986) Trends in Genetics 2:9–13). Not only can ES cells propagated in vitro contribute efficiently to the formation of chimaeras, including germline chimaeras, but in addition, these cells can be manipulated in vitro without losing their capacity to generate germ-line chimaeras (Robertson, E. J. et.al. (1986) Nature 323:445–447).

ES cells thus provide a route for the generation of transgenic animals such as transgenic mice, a route which has a number of important advantages compared with more conventional techniques, such as zygote injection and viral infection (Wagner and Stewart (1986) in Experimental Approaches to Embryonic Development. J. Rossant and A. Pedersen eds. Cambridge: Cambridge University Press), for introducing new genetic material into such animals. First, the gene of interest can be introduced and its integration and expression characterised in vitro. Secondly, the effect of the introduced gene on the ES cell growth can be studied in vitro. Thirdly, the characterised ES cells having a novel introduced gene can be efficiently introduced into embryos by blastocyst injection or embryo aggregation and the consequences of the introduced gene on the development of the resulting transgenic chimaeras monitored during pre- or post-natal life. Fourthly, the site in the ES cell genome at which the introduced gene integrates can be manipulated, leaving the way open for gene targeting and gene replacement (Thomas, K. R. and Capecci, M. R. (1987) Cell 51:503–512).

However, it is known that ES cells and certain EC (embryonal carcinoma) cell lines will only retain the stem cell phenotype in vitro when cultured on a feeder layer of fibroblasts (such as murine STO cells, e.g. Martin, G. R. and Evans, M. J. (1975) Proc. Natl. Acad. Sci. USA 72:1441–1445) or when cultured in medium conditioned by certain cells (e.g. Koopman, P. and Cotton, R. G. H. (1984) Exp. Cell Res. 154:233–242; Smith, A. G. and Hooper, M. L. (1987) Devel. Biol. 121:1–91). In the absence of feeder cells or conditioned medium, the ES cells spontaneously differentiate into a wide variety of cell types, resembling those found during embryogenesis and in the adult animal. The factors responsible for maintaining the pluripotency of ES cells have, however, remained poorly characterised.

In work leading to the present invention, it has been found that LIF has the capacity to substitute for, or be added to, feeder layers (or conditioned medium) in supporting the maintenance of pluripotential ES cells in vitro.

LIF is a protein that has previously been purified, cloned and produced in large quantities in purified recombinant form from both *Escherichia coli* and yeast cells. (International Patent Application No. PCT/AU88/00093, filed Mar. 31, 1988.) LIF has been defined as a factor, the properties of which include:
1. it has the ability to suppress the proliferation of myeloid leukaemic cells such as M1 cells, with associated differentiation of the leukaemic cells; and
2. it will compete with a molecule having the defined sequence of murine LIF or human LIF (defined in International Patent Application No. PCT/AU88/00093) for binding to specific cellular receptors on M1 cells or murine or human macrophages. In addition to the biological properties previously disclosed for murine and human LIF, LIF has now been found to have the following properties:
    (a) it allows the derivation and maintenance in the absence of feeder cells of the pluripotential phenotype in vitro of ES cells.
    (b) it allows the aforementioned ES cells, after passage in vitro in the presence of LIF, to contribute to somatic and germline cell tissues of chimaeric animals such as mice when re-introduced into the embryonic environment;
    (c) it demonstrates selective binding to high affinity receptors on murine ES (Ekcs-1 (previously known as CS1) and D3) and EC (PCC3-3A and F9) cells; and
    (d) specific binding of $^{125}$I-LIF to high affinity receptors is not in competition with insulin, IGF-I, IGF-II, acidic and basic FGF, TGFβ, TNFα, TNFβ, NGF, PDGF, EGF, IL-1, IL-2, IL-4, GM-CSF, G-CSF, Multi-CSF nor erythropoietin, but is in competition with murine and human LIF.

Accordingly, a first aspect of the present invention relates to a method for the isolation of embryonic stem (ES) cells from animal embryos in vitro which method comprises deriving ES cells from said embryos in culture medium, said culture medium containing an effective amount of leukaemia inhibitory factor (LIF), for a time and under conditions sufficient for the development of said ES cells. The embryos used may be isolated from animals including, but not limited to, humans and a number of other animal species such as birds (eg. chickens), mice, sheep, pigs, cattle, goats and fish.

A second aspect of the present invention, contemplates a process for maintaining animal embryonic stem (ES) cells in vitro while retaining their pluripotential phenotype, which process comprises culturing said cells in a culture medium containing an effective amount of leukaemia inhibitory factor (LIF) under conditions sufficient to maintain said cells. The ES cells in accordance with this aspect of the invention include cells from humans, mice, birds (eg. chickens), sheep, pigs, cattle, goats and fish.

The LIF used in the culture medium is preferably recombinant LIF produced, by way of example, in accordance with the methods described in International Patent Application No. PCT/AU88/00093. In accordance with the present invention, it has been found that recombinant LIF and in particular recombinant human and murine LIF are effective substitutes for, or additives to, feeder layers or conditioned medium in maintaining ES cells in vitro. For the purposes of the present description recombinant LIF is produced in *E. coli* and yeast using the methods described in International Patent Application No. PCT/AU88/00093, however, it is within the scope of the present invention to include recombinant LIF produced in other hosts including mammalian and insect cells and to synthetic LIF.

In another aspect, the present invention extends to ES cells derived from animal embryos by passage in a culture medium containing LIF, to such ES cells having additional genetic material inserted therein, and to chimaeric animals such as chimaeric mice or transgenic progeny of said animals generated by known techniques using ES cells which have been maintained in vitro in a LIF-containing culture medium.

Thus, the invention extends to the generation and maintenance of ES cells from humans, mice, birds (eg. chickens), sheep, pigs, cattle, goats and fish and to the generation of transgenic chimaeric animals and their transgenic progeny using the ES cells isolated from animal species such as mice, birds (eg. chickens), sheep, pigs, cattle, goats and fish. This invention also includes the use of LIF in culture media to modulate the survival and growth of human and other animal species such as cattle germ cells and embryonic cells, for example, for use in in vitro fertilisation and other procedures.

The present invention may also be described by reference to the following figures.

Figure 1:
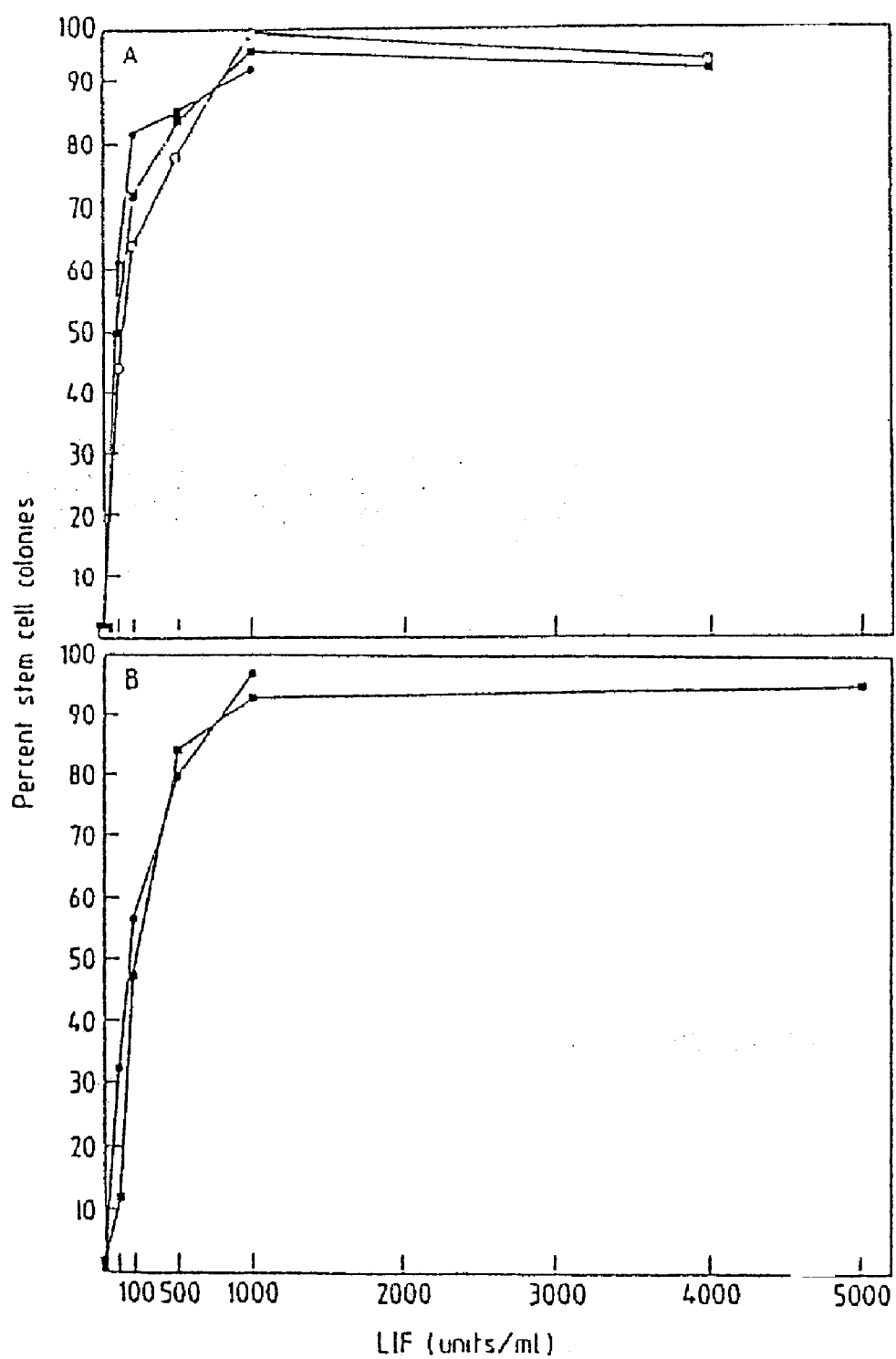
FIG. 1 is a graphical representation showing the effect on ES cells of different concentrations of LIF.

The present invention is directed to a method for the isolation and maintenance of embryonic stem (ES) cells from animal embryos in vitro which method comprises deriving and/or maintaining said ES cells from said embryos in culture medium containing an effective amount of leukaemia inhibitory factor (LIF), for a time and under conditions sufficient for the derivation and/or maintenance of said ES cells. The animal embryos may be isolated from a number of animal species such as humans, mice, birds (eg. chickens), sheep, pigs, cattle, goats and fish. By reference herein to "animal embryos" includes reference to "animal blastocysts". Furthermore, the present invention is exemplified using human LIF with murine ES cells (heterologous system) and murine LIF with murine ES cells (homologous system). This is done with the understanding that the present invention contemplates LIF from any animal species in heterologous or homologous systems with animal embryos from animal species such as humans, mice, birds (e.g. chickens), sheep, pigs, cattle, goats and fish. Although in certain circumstances, a heterologous system will work effectively, it may be preferable to use homologous systems. Given the teachings herein, it will be routine for the skilled technician to ascertain whether a homologous or heterologous system is required in order to isolate or maintain particular animal ES cells.

By "culture medium" is meant a suitable medium-capable of supporting growth of ES cells. Examples of suitable culture media useful in practicing the present invention are Eagles medium or modifications or equivalents thereof such as Dulbecco's or Glasgows modified Eagle's medium with supplements such as 5%–30% (v/v) foetal calf serum and where necessary 0.01 to 1.0 mM β-mercaptoethanol but preferably about 0.1 mm β-mercaptoethanol. The culture medium may or may not contain feeder cells and LIF may be used to substitute for, or add to, said feeder cells. When required, LIF, or ore particularly synthetic or recombinant LIF, is added to the medium at a concentration of about 100–1,000,000 units/ml and preferably about 100–100,000 units/ml and even more preferably 500–10,000 units/ml where 50 units are defined as the amount of LIF which in one milliliter induces a 50% reduction in clone formation by murine M1 myeloid cells. By "recombinant LIF" is meant the LIF prepared by genetic engineering means such as, for example, according to International Patent Application No. PCT/AU88/00093 where a number of hosts such as bacteria (eg. *E. coli*) or yeast cells may be employed. In accordance with the present invention, the effective derivation time is from 1 day to 20 weeks and particularly from 1 to 8 weeks.

Another aspect of the present invention contemplates a process for maintaining animal ES cells in vitro while retaining their pluripotential phenotype which process comprises culturing said cells in a culture medium containing an effective amount of LIF under conditions sufficient to maintain said cells. The ES cells in accordance with this aspect of the invention include cells derived from humans, mice, birds (eg. chickens), sheep, pigs, cattle, goats and fish. As with the isolation of ES cells from animal embryos, the LIF used in the aformentioned process is preferably recombinant LIF. The culture medium may or may not contain feeder cells.

In accordance with the present invention, "pluripotential cells" and "embryonic stem cells" are those which retain the developmental potential to differentiate into all somatic and germ cell lineages.

The ability of recombinant LIF to maintain the stem cell phenotype of ES cells is demonstrated by transferring ES cells D3 and HD5 into normal cell culture medium in the presence of varying concentrations of purified yeast-derived recombinant human LIF (rY-HLIF) or *E. coli*—derived recombinant mouse LIF (rE-MLIF). At concentrations of 1000–5000 units/ml of rY-HLIF or rE-MLIF more than 90% of the D3 and HD5 ES cells retained their stem cell phenotype. In contrast, the ES cells maintained in normal culture medium differentiated over a period of 3–6 days. The proportion of colonies having the stem cell phenotype was related to the concentration of LIF in the culture medium. In addition to maintaining established ES cell lines, six new ES cell lines (MBL-1,2,3,4,5 & 6) were isolated from blastocysts in the absence of feeder cells when the media was supplemented with, 1000 units/ml rE-HLIF. Long term maintenance of the ES cell lines D3, HD5 and MBL-1 to 6 in LIF for up to 22 passages (approximately 1.00 cell generations or 10 weeks) did not noticeably alter the growth characteristics of these ES cells or their dose dependency on LIF. The ability of these ES cells to differentiate into all somatic and germ cell linages was confirmed by reintroduction of D3 and MBL-1 cells into blastocysts. Approximately 50% of the progeny analysed contained tissues derived from the injected ES cells with levels of overt chimaerism as high as 90% in individual mice. To test for germline transmission of ES derived cells male chimaeras were mated to C57BL/6J mice. Three D3 and two MBL-1 C57BL/6J chimaeras gave rise to agouti progeny confirming that these ES cells can contribute to the formation of germ cells.

The present invention also relates to chimaeric animals generated by known techniques using the ES cells contemplated herein. These ES cells may be isolated from animal embryos and/or maintained in vitro according to the subject invention. Furthermore, genetically manipulated ES cells may be passaged in LIF and used to make chimaeric animals. For example, genetically manipulated ES cells containing a retrovirus vector (N-TK527; derived from pXT1; C. A. Boulter and E. F. Wagner, (1987) Nucl. Acids Res. 15:7194) encoding genes for neomycin resistance and c-src[527] were propagated in the presence of LIF but in the absence of feeder cells for over 20 passages. These cells still retained the ability to differentiate as judged by the formation of normal chimaeras following introduction of these cells into preimplantation embryos by blastocyst injection.

Further details of the use of LIF in accordance with the present invention will be apparent from the following Examples.

EXAMPLE 1

This example sets out the steps used to maintain ES cells in vitro in LIF, and to generate chimaeric mice using ES cells so passaged.

Step 1; Propagation In Vitro:

The ES cells used were the D3 (Doetschman, T. C. et.al. (1985) J. Embryol. Exp. Morphol. 87:27–45) the EKcs-1 (previously known as CS1) (Wagner, E. F. et.al. (1985) Cold Spring Harbor Symp. Quant. Biol. 50:691–700) and the HD5 (C. Stewart, unpublished) ES cell lines isolated from 129 SV He blastocysts and the CBL63 (R. Kemler, unpublished) ES cells isolated from C57BL/6J blastocysts. Prior to culture in LIF, the D3 and CBL63 cells were maintained in Dulbecco modified Eagles medium with 15% (v/v) foetal calf serum on a feeder layer of primary embryo fibroblasts, and the EKcs-1 and HD5 ES cells were maintained in Eagle's medium with 15% (v/v) foetal calf serumand 0.1 mM β-mecraptoethanol, in the presence of medium conditioned by the bladder carcinoma cell line 5637 (ATCC No. HTB9).

Figure 2:
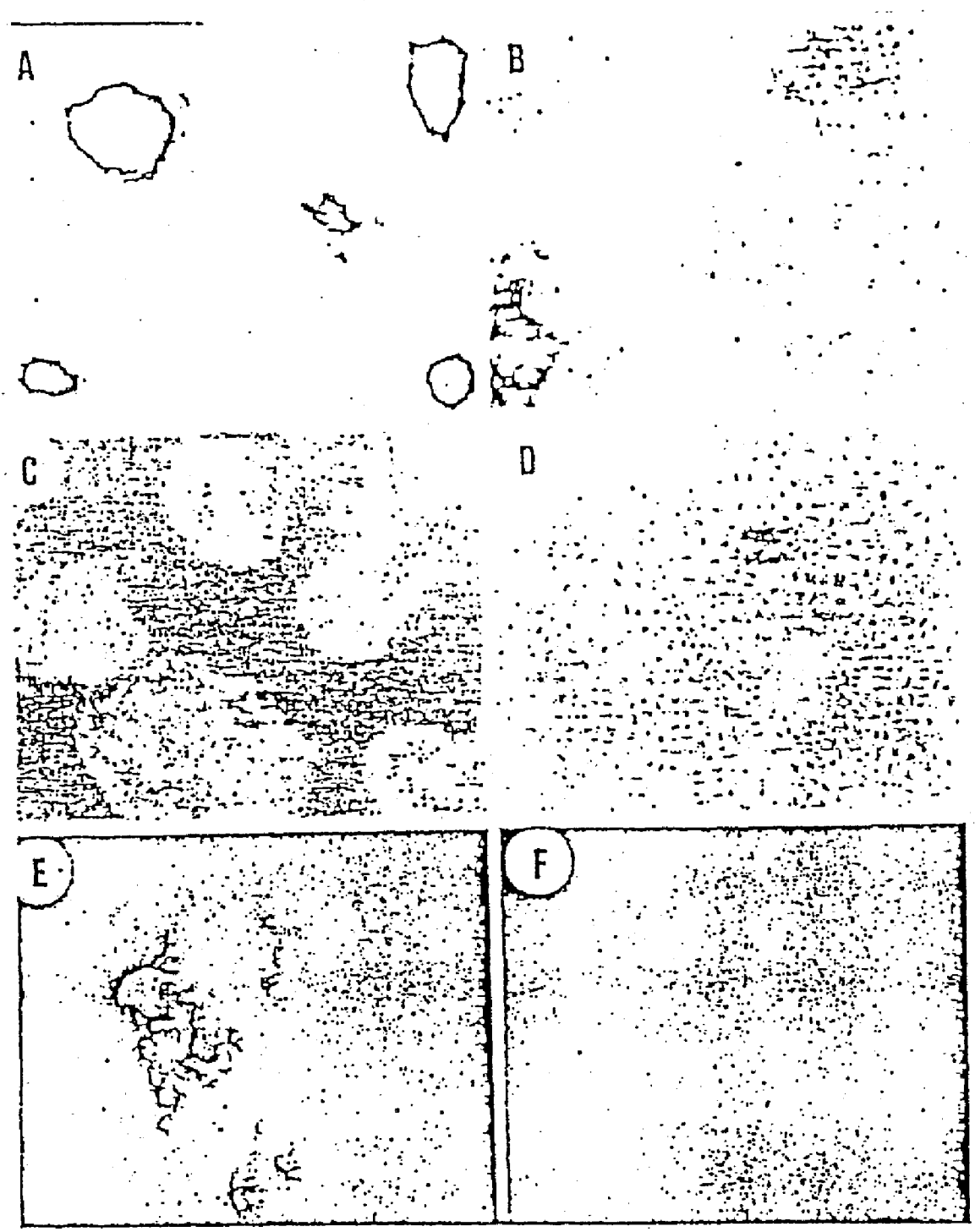
FIG. 2 is a pictorial representation showing ES cell morphology in the presence and absence of LIF.

The ability of recombinant LIF to maintain the stem cell phenotype of ES cells was demonstrated by transferring ES cells of the lines D3 and HD5 into normal cell culture medium in the presence of varying concentrations of purified yeast-derived recombinant human LIF (hereafter referred to as rY-HLIF), or *E. coli* derived recombinant mouse LIF (rE-MLIF) (previously disclosed in International Patent Application No. PCT/AU88/00093). The results are shown in FIGS. 1 and 2. In FIG. 1A, HDS cells previously maintained in 80% 5637 conditioned medium for eight passages were transferred to culture media containing 0–5,000 units ml$^{-1}$ of purified, recombinant yeast-derived human LIF (H-LIF; see below) (■—■) or purified, recombinant *E. coli*-derived mouse LIF (M-LIF; see below) (○—○). HD5 cells maintained in medium containig 1,000 units ml$^{1}$ H-LIF for a further 13 passages were then transferred to 0–1,000 units ml$^{-1}$ M-LIF (●-574 ). In FIG. 1B, D3 cells maintined on mouse embryo fibroblasts for 10 passages were transferred to media containing 1,000–5,000 units ml$^{-1}$ H-LIF and after a further 7 or 15 passages the cells were transferred into media containing 0–5,000 units ml$^{-1}$ of H-LIF (■—■) or 0–1,000 units ml$^{-1}$ M-LIF (●—●) respectively. FIG. 2 shows ES cell morphology in the presence of recombinant LIF. HD5 ES cells cultured in the presence of 80% 5637 conditioned medium were assayed for the ability of purified recombinant LIF to maintain the stem-cell phenotype by transfer to media containing 1,000 units ml$^{-1}$ M-LIF (A), or to normal culture media (B). After seven days, the colonies were stained with Giemsa. Compact stem-cell colonies could be distinguished from diffuse differentiated colonies. D3 cells maintained in H-LIF for 15 passages were assayed for the ability to differentiate by transfer into media containing 1,000 units ml$^{-1}$ M-LIF (C) or normal culture media (D). Immunofluorescence of the cells in the two D3 colony types was carried out using the ECMA-7 monoclonal antibody which recognizes a stem cell-specific cell-surface antigen. Cell-surface-specific immunofluorescence was detected on over 90% of the cells maintained in media containing 1,000 units ml$^{-1}$ recombinant LIF (E) but on less than 1% of the cells maintained in normal culture media (F). The field of view shown in (F) contains 21 cells.

FIGS. 1 and 2 indicate that over 90% of the ES cells maintained in 1000–5000 units/ml rY-HLIF or rE-MLIF retained their stem cell phenotype. In contrast, ES cells maintained in normal culture medium differentiated over a period of 3–6 days. The different concentrations of rY-HLIF or rE-MLIF used did not result in any noticeable change in cell number after 6 days in culture, indicating that there is no selection for a specific subpopulation able to grow in LIF. Similar results have been obtained using yeast-derived rMLIF also disclosed in International Patent Application No. PCT/AU88/00093. The data in Figure. I indicate that human LIF acts on mouse ES cells, as previously described for the action of human LIF on M1 myeloid leukaemic cells (Gough, N. M. et.al. (1988) Proc.Natl.Acad.Sci.USA 85: 2623–2627). The data in Figure. I also indicate that the action of LIF on ES cells is independent of glycosylation, as previously described for the action of LIF on M1 myeloid leukaemic cells.

Four ES cell lines, D3, EKcs-1, CBL63 and HD5, were maintained in medium containing 1000–5000 u/ml rY-HLIF for up to 22 passages (10 weeks or approximately 100 generations). Long-term maintenance of the ES cells in rY-HLIF did not noticeably alter the growth characteristics of the cells. Furthermore, reduction or removal of the LIF from the culture medium resulted in the differentiation of the ES cells with similar kinetics to those explanted directly from bladder carcinoma 5637 conditioned medium or a feeder layer of mouse fibroblasts (for example, see FIGS. 1 and 2). The stem cell phenotype of ES cells cultured for multiple passages in the presence of LIF was confirmed by immunofluorescence with the ECMA-7 antibody which recognises a cell-surface stem-cell-specific antigen (Kemler, R. in Progress in Developmental Biology Band 26 Sauer, H. W. ed page 175; Fisher, Stuttgart, 1980); ES cells cultured in the presence of LIF expressed the stem cell marker, whereas in the absence of LIF less than 1% did so (FIG. 2).

Step 2; Isolation of ES Cell Lines:

Murine blastocysts were isolated from 129 Sv He mice at day 4 of development (day 1=day of plug) into either Dulbecco's or Glasgows modified Eagle's medium with 15% (v/v) foetal calf serum; 0.1 mM β-mercaptoethanol and 1000 units/ml of purified rE-HLIF. ES cell lines were then isolated by two different methodologies.

In the first method the blastocysts were allowed to attach to the culture dish and approximately 7 days later the outgrowing inner cell mass picked, trypsinised and transfered to another culture dish in the same culture media. ES cell colonies appeared 2–3 weeks later with between 5–7 individual colonies arising from each explanted inner cell mass. The ES cell lines were then expanded for further analysis. The second method for isolation of ES cell lines used the immunosurgery technique (described in Martin, G. R. (1981) Proc. Natl. Acad. Sci. USA 78:7634–7638) where the trophectoderm cells are destroyed using anti-mouse antibodies prior to explanting the inner cell mass. The efficiency of ES cell lines isolation is shown in Table 1.

Step 3; Generation of Chimaeric Mice:

All the ES cell lines cultured in the absence of feeder cells but in the presence of LIF (referred to in step 1) or directly isolated with the aid of culture medium containing LIF (referred to in step 2) retained the ability to differentiate into multiple cell types following the removal of LIF indicating that these cells have retained their pluripotential phenotype. To confirm their developmental potential, D3 ES cells maintained in LIF for 7–22 passages and MBL-1 ES cells maintained in LIF for 14–17 passages were reintroduced into the embryonic environment by blastocyst injection (as described in Williams et al., (1988) Cell 52:121–131). Blastocysts were isolated from the outbred ICR mouse strain or inbred C57BL/6J mice. The expanded blastocysts were maintained in oil-drop cultures at 4° C. for 10 min prior to culture. The ES cells were prepared by picking individual colonies, which were then incubated in phosphate-buffered saline, 0.5 mM EGTA for 5 min; a single cell suspension was prepared by incubation in a trypsin-EDTA solution containing 1% (v/v) chick serum for a further 5 min at 4° C. Five to twenty ES cells (in Dulbecco's modified Eagle's Medium with 10% (v/v) foetal calf serum and 3,000 units/ml DNAase 1 buffered in 20 mM HEPES [pH 8]) were injected into each blastocyst. Blastocysts were transferred into pseudopregnant recipients and allowed to develop normally. Chimaeric mice were identified by coat markers (Hogan et al., (1986) Manipulating the Mouse Embryo, Cold Spring Harbor, N.Y.). Analysis of the subsequent chimaeric mice revealed that up to approximately 50% of the progeny contained tissues derived from the injected cells (Table 2), with levels of overt chimaerism as high as 90% in individual mice. Furthermore analysis of the organs of four D3-chimaeras confirmed that the ES cells maintained in LIF could contribute extensively to the development of all of the somatic tissues (Table 3).

The male chimaeras were tested for germline transmission of ES derived cells by mating to ICR or C57BL/6J females. Three out of four of the D3-C57BL/6J chimaeras and two out of six of the MBL-1-C57BL/6J chimaeras gave rise to agouti offspring derived from the ES cells cultured in LIF (Table 4).

To test whether genetically altered ES cells could be maintained in culture medium containing LIF, D3 ES cells were infected with a retrovirus vector (N-TK527) expressing the neomycin resistance gene and a c-src gene mutant (c-src$^{527}$) (protocol for infection is described in Williams et al., (1988) Cell 52: 121–131). The ES cell clones isolated were maintained in culture medium containing LIF for over 20 passages. These genetically modified ES cells retained the ability to form chimaeric mice following reintroduction into the embryonic environment by blastocyst injection (Table 2)

TABLE 1

Isolation of 129 Sv He ES cell lines in media containing rE-HLIF

| Methodology | Blastocyst | ICM outgrowing | Number of ES cell lines derived |
|---|---|---|---|
| Explanted | 9 | 9 | 4 |
| Immunosurgery | 11 | 3 | 0 |
| Immunosurgery | 7 | 5 | 2 |

Murine blastocysts were isolated from 129 Sv He mice at day 4 of development (day 1=day of plug) into either Dulbecco's or Glasgows modified Eagle's medium with 15% (v/v) foetal calf serum, 0.1 mM β-mercaptoethanol and 1000 units/ml of purified rE-HLIF. The blastocysts were then explanted into the same media and left to attach to the culture dish and the inner cell mass picked dissociated in phosphate-buffered saline, 0.5 or EGTA for 5 min; a single cell suspension was prepared by incubation in a trypsin-EDTA solution containing 1% (v/v) chick serum and the cells replated in the cell culture medium described above. The characteristic ES cell colonies appeared within 1–3 weeks.

Other blastocysts were treated by immunosurgery (as described in Martin, G. R. (1981) Proc. Natl. Acad. Sci. USA 78:7634–7638). The blastocysts were allowed to hatch from the zona pelucida, and then treated with anti-mouse antibodies and destroyed by the addition of complement. The exposed inner cell mass was then left to, attach to a tissue culture dish and again treated with anti-mouse antibodies and complement. Within a few days pluripotential stem cell colonies appeared and were dissociated and trypsinised as described above.

TABLE 2

Chimaeric mice derived from ES cells cultured in LIF

| ES cells | Blastocysts transferred | Pups born | Chimaeras |
|---|---|---|---|
| D3 | 142 | 60 (42%) | 33 (55%) |
| MBL-1 | 51 | 33 (65%) | 16 (48%) |
| D3 N-TK527 | 42 | 22 (52%) | 12 (54%) |

TABLE 3

Percentage tissue contributions in individual D3 chimaeric mice

| Chimaera | Necropsy age | C | Bl | Sp | P | Li | T | H |
|---|---|---|---|---|---|---|---|---|
| D3-1 | 13 d | 35 | 0 | 35 | 20 | 10 | 20 | 40 |
| D3-2 | 14 d | 40 | 15 | 35 | 30 | 45 | 30 | 50 |
| D3-3 | 11 d | 90 | 50 | 50 | 35 | 50 | 40 | 60 |
| D3-4 | 11 d | 50 | 50 | 50 | 30 | 40 | 40 | 50 |

| Chimaera | Necropsy age | Lu | G | K | M | B | Sa |
|---|---|---|---|---|---|---|---|
| D3-1 | 13 d | 30 | 10 | 35 | 30 | 35 | 20 |
| D3-2 | 14 d | 35 | 20 | 30 | 50 | 50 | 25 |
| D3-3 | 11 d | 45 | 50 | 50 | 70 | 50 | 55 |
| D3-4 | 11 d | 50 | 35 | 50 | 50 | 20 | 30 |

TABLE 4

Chimaeric demonstrating germline transmission of ES derived cells.

| | | Passage no. of D3 cells | | Offspring | |
|---|---|---|---|---|---|
| Mice | Chimaerism | on feeders | in LIF | 129 Sv He | C57 |
| 775-3 | 75% | 10 | 16 | 9 | 24 |
| 778-1 | 70% | 10 | 22 | 5 | 33 |
| 778-2 | 50% | 10 | 22 | 2 | 36 |
| 778-3 | 55% | 10 | 22 | 0 | 0 |

The Following Relates to Tables 2, 3 and 4:

D3 and M8l-l ES cells are derived from 129 Sv He mice (inbred, agouti, homozygous for the glucose phosphate isomerase $1^a$ allele). The D3 ES cells were originally cultured on primary embryo fibroblasts for 10 passages and then transferred to 1,000–5,000 units/ml recombinant LIF for 7–22 passages. The MB1-1 ES cells were isolated in the absence of feeder cells but in the presence of rE-HLIF these cells were cultured for 14–17 passages. The ES cells were then injected into ICR (outbred, albino) or C57BL/6J (inbred, black) blastocysts which were then transfered into pseudo-pregnant foster mothers. Both the ICR and C57BL/6J mice are homozygous for the glucose phosphate isomerase $1^b$ allele. Chimaeric pups were identified by coat pigmentation (only foster mothers which became pregnant were counted in estimating the number of progeny). Tissue chimaerism was estimated using glucose phosphate isomerase strain differences. The extent of tissue chimaerism was determined in two D3-ICR (numbers 1 and 2) and two D3-C57BL/6J chimaeras (numbers 3 and 4). Tissues analysed: C, coat; Bl, blood; Sp, spleen; P, pancrease; Li, liver; T, thymus; H, heart; Lu, lungs; G, gonads; K, kidneys; M, muscle; B, brain; Sa, salivary gland. Male chimaeras were mated to ICR or C57BL/GJ mice and offspring identified by coat pigmentation.

EXAMPLE 2

Figure 3:
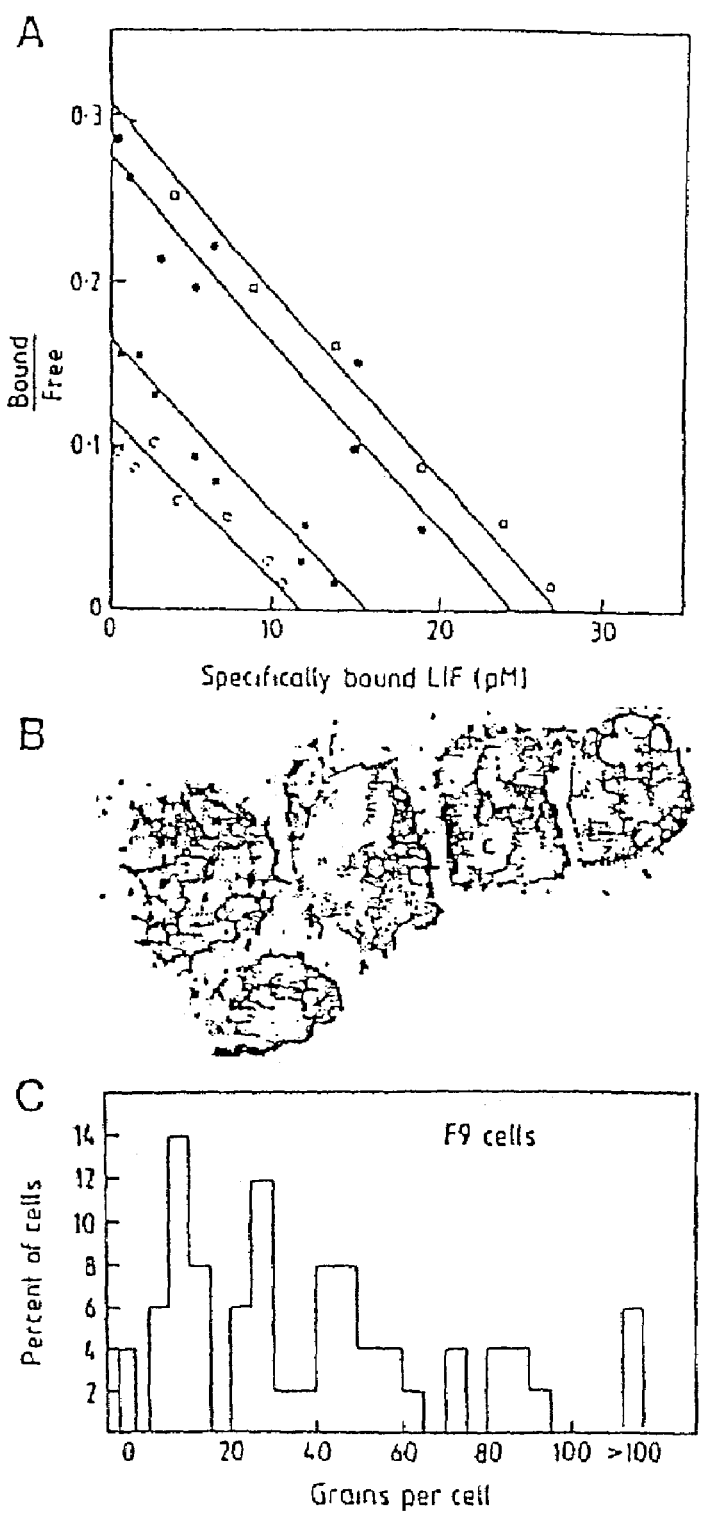
FIG. 3 is a graphical (A and C) and pictorial (B) representation showing the binding of $^{125}$I-LIF to ES cells (EKcs-1) and EC cells (F9 and PCC3-A).

This example sets out the steps used to document specific high affinity receptors on ES and EC cells. Accompanying FIG. 3 shows binding of $^{125}$I-LIF to ES cells EKcs-1 and EC cells F9 and PCC3-A (Jakob, J. et.al. (1973) Ann. Microbiol. Inst. Pasteur, 124B: 269–282). In relation to FIG. 3, (A), Scatchard analysis of $^{125}$I-labelled LIF binding to F9 (□), EKcs-1 (●), PCC3A-1 (■) and M1 (○) cells. Saturation curves for binding were analysed by the method of Scatchard by plotting the amount of LIF specifically bound (defined as the difference between binding observed in the absence and presence of excess unlabelled LIF) versus the ratio of bound to free LIF. Free LIF values were adjusted for the percent of $^{125}$I-labelled LIF capable of binding specifically to LIF receptors, in this experiment determined to be 75%. The apparent dissociation constant for the interaction of LIF with its receptor was determined from the slopes of the curves and the receptor number from their intercepts with the ordinate. Results in (A) were standardized to $5\times10^6$ cells per point and the mean of duplicate points are shown and curves were fitted using the Ligand program. (B), Autoradiography of F9 EC cells labelled with $^{125}$I-labelled LIF. (C), Quantitation of silver grains on F9 EC cells after binding of $^{125}$I-labelled LIF.

Purified recombinant (yeast-derived) human LIF (rY-HLIF) was radioactively labelled on tyrosine residues as described previously (Hilton, D. J. et. al. (1988) Proc. Natl. Acad. Sci. USA, 85:5971–5975) producing $^{125}$I-LIF with a specific radioactivity of approximately $1.2\times10^7$ cpm/pmole. $^{125}$I-LIF ($2\times10^3$–$5\times10^5$ cpm) was incubated with 1–$4\times10^6$ target cells with or without at least 100-fold molar excess of unlabelled LIF, in a total volume of 100 μl for 4 hours on ice. Cell-associated and free $^{125}$I-LIF were separated by centrifugation through foetal calf serum (Nicola, N. A. and Metcalf, (1986) D. J. Cell Physiol. 128:160–188). Specific cell-associated $^{125}$I-LIF was determined by cold competition.

FIG. 3 illustrates the specific saturable and high affinity binding of $^{125}$I-LIF to the ES cells EKcs-1 and the EC cells PCC3-A and F9. The number of LIF receptors per cell derived from these Scatchard plots were 295, 190 and 330, respectively, with apparent dissociation constants at 4° C. of approximately 90 pM. This compares with the M1 cell line, a LIF-responsive monocytic leukaemia, which displays 50–200 LIF receptors/cell with an apparent dissociation constant of 50–150 pM. All other ES and EC cells tested—D3, NG2, PC13 and P19—bound similar levels of LIF (data not shown).

The binding of $^{125}$I-LIF to M1 cells, EKcs-1 and PCC3-A was also found to be in competition with unlabelled recombinant and native murine and human LIF, but not with the range of other hormones and factors, (including several which act on embryonic cells): insulin, IGF-I, IGF-I, acidic and basic FGF, TGFβ, TNFα, TNFβ, NGF, PDGF, EGF, IL-1, IL-4, GM-CSF, G-CSF, Multi-CSF and erythropoietin.

The invention claimed is:

1. A method of producing a genetically modified mouse, comprising culturing murine embryonic stem (ES) cells in culture medium containing an effective amount of recombinant leukaemia inhibitory factor under conditions sufficient to maintain said ES cells and producing a genetically modified mouse using said ES cells.

2. A method of producing a genetically modified mouse, comprising culturing murine embryos in vitro in culture medium containing an effective amount of recombinant leukaemia inhibitory factor for an effective time and under conditions sufficient for the development of embryonic stem (ES) cells and producing a genetically modified mouse using said ES cells.

3. The method according to claim 1 or claim 2, further comprising isolating said ES cells and producing said genetically modified mouse from said isolated ES cells.

4. The method according to claim 1 or claim 2 wherein the culture medium is free of feeder cells.

5. The method according to claim 1 or claim 2 wherein said leukaemia inhibitory factor is recombinant human or murine leukaemia inhibitory factor.

6. The method according to claim 1 or claim 2, further comprising producing progeny from said genetically modified mouse wherein said progeny comprises the genetic modification of said genetically modified mouse.

* * * * *